United States Patent [19]

Rotman

[11] Patent Number: 4,559,299
[45] Date of Patent: Dec. 17, 1985

[54] CYTOTOXICITY ASSAYS IN CELL CULTURING DEVICES

[75] Inventor: M. Boris Rotman, Jamestown, R.I.

[73] Assignee: Brown University Research Foundation Inc., Providence, R.I.

[21] Appl. No.: 463,669

[22] Filed: Feb. 4, 1983

[51] Int. Cl.$^4$ .................. C12Q 1/29; C12Q 3/00; C12N 5/00; C12N 5/02; C12M 3/00; C12M 1/00; C12M 1/34; G01N 33/54

[52] U.S. Cl. .................................... 435/29; 435/3; 435/4; 435/240; 435/241; 435/284; 435/287; 435/291; 435/808; 435/810; 435/811; 436/4; 436/34; 436/63; 436/68; 436/178; 422/48; 422/61; 422/68

[58] Field of Search .................. 435/3, 4, 29, 32, 34, 435/240, 241, 284, 287, 291, 808, 810, 811; 436/4, 34, 63, 68, 172, 178; 422/48, 61, 68

[56] References Cited

U.S. PATENT DOCUMENTS

| 2,996,426 | 8/1961 | Toulmin | 514/122 |
|---|---|---|---|
| 3,476,514 | 11/1969 | Roth | 436/64 |
| 3,586,859 | 6/1971 | Katz | 240/459.1 |
| 3,657,537 | 4/1972 | Wheeless, Jr. et al. | 250/461.2 |
| 3,821,087 | 6/1974 | Knazek et al. | 435/284 |
| 3,853,712 | 12/1974 | House et al. | 435/284 |
| 3,883,393 | 5/1975 | Knazek et al. | 435/284 |
| 3,948,732 | 4/1976 | Haddad et al. | 435/284 |
| 4,184,922 | 1/1980 | Knazek et al. | 435/284 |
| 4,201,845 | 5/1980 | Feder et al. | 435/284 |
| 4,220,725 | 9/1980 | Knazek et al. | 435/284 |
| 4,225,229 | 9/1980 | Gohde | 356/39 |
| 4,241,187 | 12/1980 | White | 435/284 |
| 4,308,351 | 12/1981 | Leighton et al. | 435/284 |
| 4,343,782 | 8/1982 | Shapiro | 424/3 |

FOREIGN PATENT DOCUMENTS 0916373 1/1963 United Kingdom .................. 435/40

OTHER PUBLICATIONS

Maeda et al., Chemical Abstracts, v. 97, Abstract No. 155804s 1982, pp. 7–8, "Investigation of Factors Involved in the Uptake Velocity of Fluorescein Diacetate and Intracellular Fluorescecen Polarization Value II Cytotoxicity Produced by Anticancer Agents."

Liess, Bernd, Chemical Abstracts, v. 82, Abstract No. 53792j, 1975, pp. 249–250, "Apparatus for Cell Culturing and Treatment."

Knazek, Richard A., Fed Proc., v. 33, No. 8, 1974, pp. 1978–1981, "Solid Tissue Masses Formed in Vitro From Cells Cultured on Artificial Capillaries."

Rotman, Boris & Papermaster, Ben W., "Membrane Properties of Living Mammalian Cells as Studied by Enzymatic Hydrolysis of Fluorogenic Esters", Proceedings of the National Academy of Sciences, vol. 55, No. 1, pp. 134–141, Jan. 1966.

Morris, N. G. & Leibovitz, A., Quartles, "Hemodialysis-Matrix Perfusion Culture System: A New Technique for Studying Chemotherapeutic Activity Against Tumor Cells."

Salmon, Sydney E. et al., The New England Journal of Medicine, vol. 298, pp. 1321–1327, (Jun. 15, 1978), "Quantitation of Differential Sensitivity of Human-Tumor Stem Cells to Anticancer Drugs."

Buick et al., Cancer Research, vol. 39, pp. 5051–5056 (1979) "Development of an Agar-Methyl Cellulose Clonogenic Assay for Cells in Transitional Cell Carcinoma of the Human Bladder."

Von Hoff et al., Cancer, vol. 50, pp. 696–701 (1982), "Direct Cloning of Human Malignant Melanoma in Soft Agar Culture."

Schratter, Method in Cell Biology, vol. XIV, pp. 95–103 (1976) "Cell Culture with Synthetic Capillaries."

Primary Examiner—Thomas G. Wiseman
Assistant Examiner—Robin Lyn Teskin

[57] ABSTRACT

Methods and devices for assaying the sensitivity of of biopsied cells to therapeutic agents are disclosed. Cells are cultured in artificial organs and then contacted with a fluorogenic substrate such that living cells accumulate a characteristic amount of fluorescence. The agent is then introduced into the organ and changes in the fluorescence released by the cells serve as an indicator of the sensitivity of the cells to the agent.

10 Claims, 5 Drawing Figures

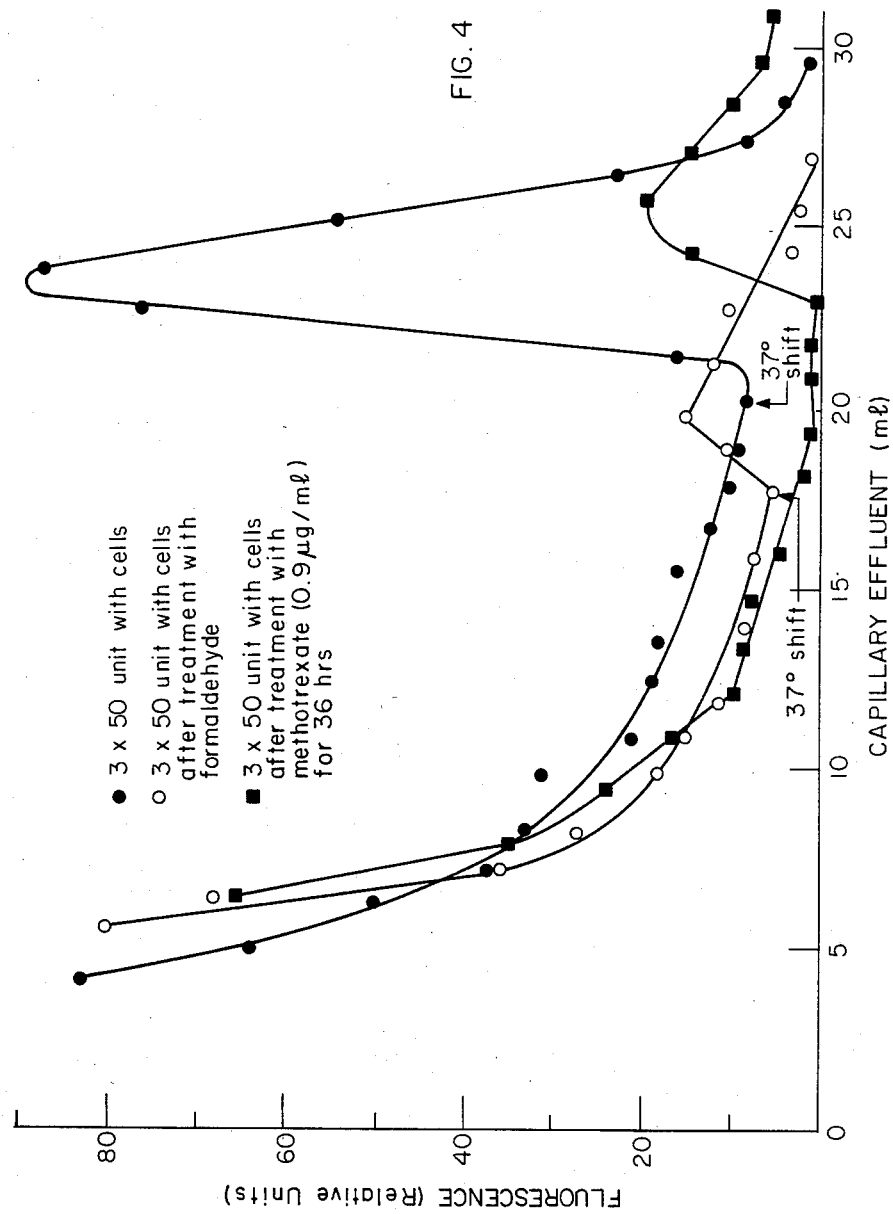

CYTOTOXICITY ASSAYS IN CELL CULTURING DEVICES

TECHNICAL FIELD

This invention relates to methods and devices for predicting the in vivo responsiveness of abnormal cells to cytotoxic agents based on in vitro culture asessments.

BACKGROUND OF THE INVENTION

It is known that cancerous or otherwise abnormal cells of identical histopahtological type show a wide range of responsiveness to particular drug therapies among individual patients. Predictive techniques, similar to the culture and sensitivity assays used for the management of microbial infections, would be of great assistance in selecting effective chemotherapy for individual cases.

Without individualized anti-cancer drug regimens, practitioners are forced to rely on past experience or reports on similar cell disorders or trial-and-error procedures. With the increasing number of anti-cancer agents available and the limited time often available for modifying doses or agents, the task of selecting the optimal regimen, without the aid of predictive assays, is very difficult.

A number of predictive systems have been proposed. See, for example, Salmon et al., "Quantitation of Differential Sensitivity of Human Stem Cells to Anti-Cancer Drugs," Vol. 298 *New England Journal of Medicine* pp. 1321-1327 (1978). Typically, the prior art techniques involve the cloning of single cell suspensions from biopsy specimens in soft agar after brief exposure to particular anit-cancer drugs. See also, Buick et al., "Development of an Agar-Methyl Cellulose Clonogenic Assay for Cells in Transitional Cell Carcinoma of the Human Bladder," Vol. 39 *Cancer Research* pp. 5051-5056 (1979) and Von Hoff et al., "Direct Cloning of Human Malignant Melanoma in Soft Agar Culture," Vol. 50 *Cancer* pp. 696-701 (1982), for further details on agar culture techniques.

Various difficulties limit the usefulness of agar culture studies for predicting the effectiveness of cytoxic agents against abnormal cells. Only a small fraction of biopsied cancer cells grow in soft agar. For example, when cell suspensions from myeloma specimens are plated in agar, plating efficiencies of 1:1000 are not uncommon. Thus, for statistically significant results comparing different drugs at different doses, large number of cells are required. It is also not certain that colonies formed in agar will be derived from the most malignant tumor cells. Moreover, agar techniques typically limit drug exposure to a relatively brief period (i.e., one hour) prior to plating while the cell is suspended in a physiological solution. Neither the exposure technique nor the subsequent growth in agar accurately mimic in vivo conditions. Additionally, the time required for evaluation is long (i.e., 14 to 30 days) compared to the often urgent need to establish a protocol for therapy. Finally, measurements of drug sensitivity by counting cell colonies can be subjective, statistically inaccurate and time consuming.

Another predictive system which has been proposed for chemotherapy studies involves the use of cell cultures grown in an artificial organ made of a matrix of synthetic capillaries. Quartles et al., "Hemodialysis-Matrix Perfusion Culture System: A New Technique for Studying Chemotherapeutic Activity Tumor Cells," Vol. 16 In Vitro 246 (1980), report the effect of one anti-cancer agent on tumor cells grown in an artificial organ system (Amicon-Vitafiber (R)). Following exposure to the drug, the cultured cells were removed from the organ and assayed for total and viable cells, colony forming ability and growth in soft agar.

Synthetic capillary systems have advantages over soft agar techniques in presenting a culture more similar to the in vivo environment and permitting the introduction of drugs into the culture via the capillaries in a fashion more like the perfusion of active agents in a patient. For a review of capillary cultures, generally, see Schratter, "Cell Culture with Synthetic Capillaries," Vol. XIV *Methods in Cell Biology* pp. 95-103 (1976), herein incorporated by reference.

The capillary technique for studying chemotherapeutic activity reported by Quartles, supra, is still subject to many of the same problems that limit the usefulness of agar studies. Quartles and his co-workers had to remove the cells from the capillary system in order to count total and viable cells. In practice, removing cells without damage from a capillary matrix is an ardent task. Typically, the cells are removed from the capillary matrix by enzyme treatment but this treatment can be more effective on dead cells than on living cells and quantitiative results are difficult to obtain. Moreover, the culture is lost after enzyme treatment and can not be used again.

Additionally, once the cells are removed, counting viable cells under a microscope again can be subjective and inaccurate and certainly is time consuming. A drug sensitivity test which relies on visual observations of live cells is very unlikely to find widespread clinical application.

There exists a need for simple, efficient methods and apparatus for predicting the in vivo responsiveness of cancerous and otherwise abnormal cells to the therapeutic agents. The predictive culture system should be easily innoculated while cell growth and drug exposure should mimic closely the human environment. More importantly, the drug sensitivity should be quantifiable by a simple and accurate method in a relatively short time and preferably in a way that would permit a clinician to obtain a reading on the effectiveness of a particular agent without destruction of the culture so that the effects of a multi-step protocol (i.e., varying in agents or doses) can be measured sequentially.

SUMMARY OF THE INVENTION

A simple, sensitive, cytotoxicity assay capable of widespread clinical application is disclosed. The method claimed herein permits the clinician to assess cell viability in an artifical organ. The number of living cells in the organ is evaluated by measuring the retention of fluorescein or a similar label by the cell membranes. In a preferred embodiment the cultured cells are allowed to accumulate fluorescein through fluorochromasia.

Specifically, fluorochromasia occurs when a fluorogenic substrate, typically a nonpolar fluorogenic substrate such as an ester of fluorescein and an aliphatic acid, is introducted into a cell culture. The fluorogenic substrate penetrates the cell membranes where it is enzymatically hydrolyzed, liberating fluorescein and staining the cell brightly fluorescent under blue light. Since fluorescein, a negatively charged molecule, does not diffuse readily across the cytoplasmic membrane of normal cells, the process causes intracellular accumulation of fluorescein. See, generally, an article by the inventor and another entitled "Membrane Properties of Living Mammalian Cells as Studied by Enzymatic Hydrolysis of Fluorogenic Esters", Vol. 55, No. 1, *Proceedings of the National Academy of Sciences* pp. 134–141 (1966). However when a dead cell is treated with the fluorogenic substrate, no intracellular accumulating of fluorescein is observed. Therefore, if the cells in the artificial organ have been killed by an agent prior to the introduction of a fluorescent substrate, hydrolysis of the substrate will not result in intracellular fluorescein accumulation. Thus, my method of measuring the responsiveness of cell cultures to cytotoxic agents resides in monitoring changes in the rate of fluorescein released by the cultured cells.

In one aspect my invention consists of an apparatus, i.e., an artificial organ, for culturing biopsied cells. The organ includes at least one perfusion capillary or membrane surface and is preferably structured so that it may be innoculated with undissociated fragments of biopsied tissues, thus retaining the basic cellular composition of the tumor (many tumors have been shown to exhibit cellular heterogeneity). The perfusion of oxygen and nutrients as well as the three dimensional structure of the artificial organ make it likely that even tumor cells unable to grow in agar will proliferate. Moreover, given the sensitivity of fluorescence detection devices, the organ may be designed to accept small numbers of cells, thus permitting more simultaneous studies from biopsy specimens of limited size, such as colon cancer biopsies or infant cell biopsies.

In another aspect my invention encompasses a system for performing cytotoxicity stuides including a culture medium or organ wherein the biopsied cells may be grown, means for providing oxygenated nutrients to the organ, means for introducing the fluorogenic substrate into the organ, means for introducing anti-cancer agents into the organ and means for measuring the released fluorescence. Preferably, fluorescence is measured by a fluorimeter and the data collected automatically and evaluated by a computer shortly after innoculation of the organ with the anti-cancer agent. Although my invention can be practiced with a single-purpose machine, clinics with fluorimeters and general-purpose computers could also employ my system by obtaining kits containing the culture organ and fluorogenic substrates.

Moreover, although my preferred embodiment is one in which the culture organ has a limited number of perfusion capillaries or surfaces and is designed for innoculation with a small number of biopsied cells, other cell culturing devices can be substituted. See for examples of cell culturing devices: U.S. Pat. No. 3,821,087 issued to Knazek et al. on June 28, 1974 for Semi-Permeable Membranes; U.S. Pat. No. 3,853,712 issued to House on Dec. 10, 1974 for Cell Culture Systems; U.S. Pat. No. 3,948,732 issued to Haddad et al. on Apr. 6, 1976 for Cell Culture Assembly; U.S. Pat. No. 4,184,922 issued to Knazek et al. on Jan. 22, 1980 for Woven Capillary Bundles; U.S. Pat. No. 4,201,845 issued to Feder et al. on May 6, 1980 for Cell Culture Reactor; U.S. Pat. No. 4,220,725 issued to Knazek et al. on Sept. 12, 1980 for Capillary Device; U.S. Pat. No. 4,241,187 issued to White on Dec. 23, 1980 for Apparatus for Tissue Culture; and U.S. Pat. No. 4,308,351 issued to Leighton on Dec. 29, 1981 for Growing Tissue System, the teachings of these references are herein incorporated by reference.

The method of my invention may be practiced in a variety of ways. With chemotherapeutic agents that exhibit rapid action, the organ can be innoculated and the culture which grows thereon can then be perfused with a fluorogenic substrate until the cells become highly fluorochromatic (about 15 minutes). The perfusion then reverts to growth medium and the efflux of fluorescein from the cells is monitored until a steady state condition is reached. Next, the rapid action agent is introduced into the organ (either directly or by perfusion) and the cytotoxic effects immediately measured by changes in the efflux.

Alternatively, with agents exhibiting delayed (i.e., radiomimetic) effects, more detailed records of the kinetics and fluorescence of the efflux would be obtained for the organ following each of a series of perfusions with fluoroganic substrate. The slower agent would then be introduced into the organ for a given length of time (which may vary from minutes to days). Next the perfusion of fluorogenic substrate is repeated and variations from the base-line readings of fluorescence kinetics measured to determine the number of living cells remaining in the organ and, hence, sensitivity to the drug. It should be clear that these two techniques can be used in conjunction or modified in a number of ways without departing from my fundamental teachings.

The various therapeutic or chemical agents which may be tested according to my invention for effectiveness on individual cell cultures include: adriamycins, mitomycins, actinomycins, neomycins, vincristine, vinblastine, chlorambucil, cis-platinum, 6-mercapto purine, methotrexate, cyclophosphamide, melphalen, carmustine, methyl ester DOPA, BCNU, DTIC, 5-fluoruracil, m-AMSA, mitoxantrone, methyl GAG, acivicin, thymidine, hormones, antibodies, prostaglandins and lymphokines as well as X-rays or other agents as they become available.

The efflux of fluorescent material from the organ can be measured by samples taken from the return stream of the perfusion network (since the fluorescent materials will pass through the capillaries or membranes) or by sampling the cell compartment directly. In practice it has been found that readings of fluorescence may be up to four times stronger in samples taken directly from the cell compartment. My method permits a clinician to test the effects of prolonged, different combinations and programmed schedules of drugs. Additionally, with my system if a drug gives a negative cytotoxicity test, the artificial organ may serve for subsequent drug testing. Moreover, one may choose to measure fast or slow release of fluorescein by using fluorogenic substrates synthesized with different fluorescein derivates. For example, using fluorescein diacetate the half-life of intracellular fluorescence is about 45 minutes (at 37° C.) while with 6-carboxyfluorescein diacetate the half-life is extended to more than 8 hours. Temperature also has a modulating effect on fluorochromasis and, therefore, may be used to control the fluorescein efflux. For a tabulation of various fluorescein derivatives and their comparative kinetics, see the discussion in Rotman and Papermaster, supra, Vol. 55 *Proc. Nat. Acad. Sci.* pp. 134–141 (1966). In a similar manner, other fluorogenic compounds can be employed.

The invention will next be described in connection with certain preferred embodiments and experimental results; however, it should be clear that various changes and modifications can be made without departing from the spirit and scope of the claims. For example, while my preferred embodiment involves the innoculation of the culture organ with undissociated fragments of biospied tissue, single cell suspensions also may be used to innoculate the culturing organ.

Additionally, a wide variety of commercially available growth media from companys such as Gibco Corporation and others may be employed as nutrients. These media are sold under names such as Dulbecco's Modified Eagle Medium (DMEM), Roswell Park Medium (RPMI) and Minimal Eagle Medium (MEM) and typically consist of amino acids, salts, vitamins, blood serum and other nutrients. Alternatively, in clinical applications, it may be preferred to use serum from the biopsied patient for all or part of the growth medium in order to further mimic in vivo exposure to the agents undergoing testing.

Moreover, while a primary objective of this invention is to present methods and apparatus for predicting the responsiveness of cancer cells to chemotherapeutic agents, other uses may also prove valuable. For examples, drugs against other cell abnormalities may also be tested and my method may also be used in assessing the effects of drugs on non-cancerous cells as a measure of the side-effects that a particular course of chemotherapy would cause in the patient. Additionally, in the event that artificial organs become feasible as implantable substitutes for human organs rather than just cell culturing vessels, my invention provides an ideal method for testing such organs prior to implantation.

BRIEF DESCRIPTION OF THE DRAWINGS

FIG. 4 is a graph of fluorescent activity for a cell culture before and after treatment with cytotoxic agents according to the invention.

DETAILED DESCRIPTION OF THE PREFERRED EMBODIMENTS

Figure 1:
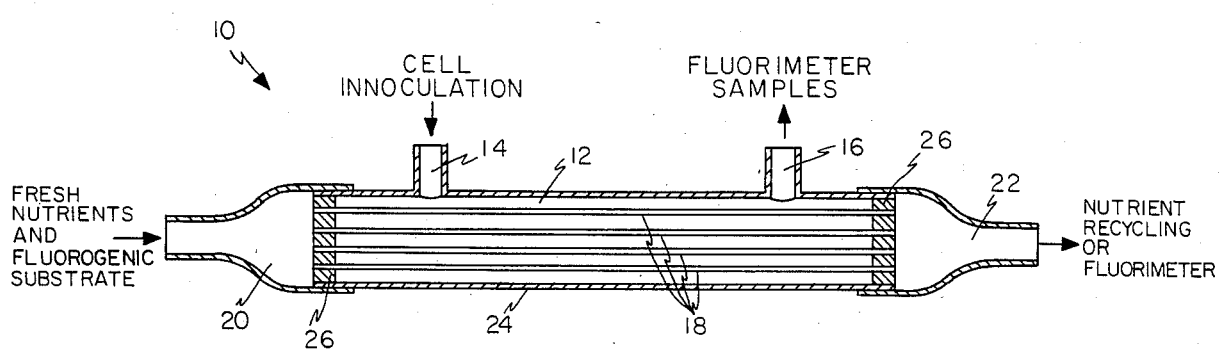
FIG. 1 is a schematic drawing of a cell culturing organ which may be employed in my invention.

With reference to FIG. 1, a culturing apparatus or organ 10 is shown comprising a cell compartment 12, capillaries 18 and shell 24. The capillaries 18 are sealed to the shell 24 by sealing means 26. In operation cells may be innoculated into the organ 10 via port 14 and washed out via port 16 (or a single port could also be used) while a growth medium and agents pass from inlet 20 to outlet 22 via the capillaries 18.

Figure 2A:
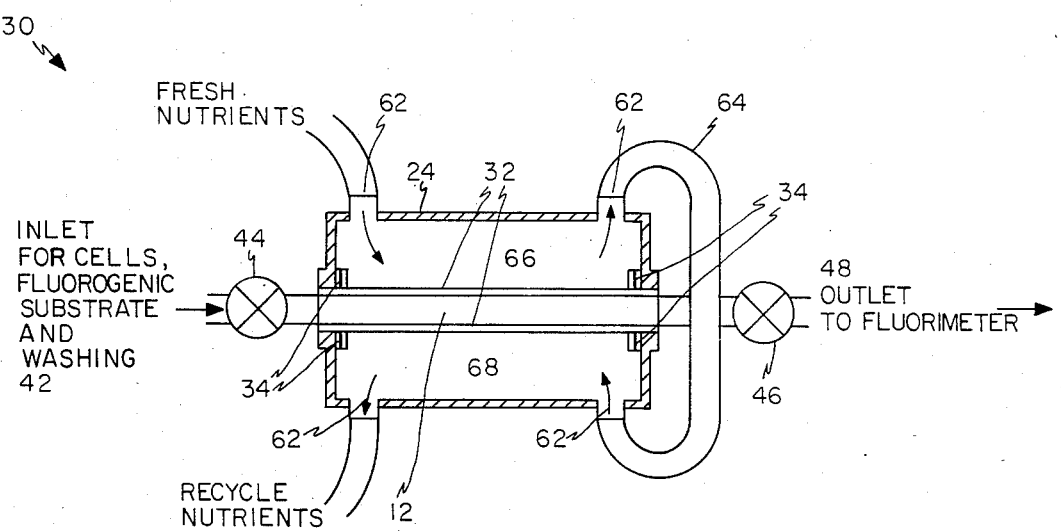
FIGS. 2a and 2b are schematic side and top drawings of an alternative cell culturing organ which may be employed in my invention.
Figure 2B:
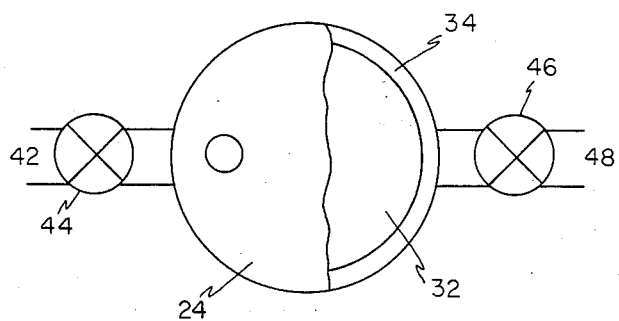

In FIG. 2 an alternative organ 30 is shown with a cell compartment 12 surrounded by two flat membrane sheets 32 and a shell 24. The membrane sheets 32 are sealed to the shell 24 by sealing rings 34. Supports or cappiliaries (not shown) may be inserted in compartment 12 to keep the membranes apart and supply extra nutrients. In operation, cells, as well as fluorogenic substrate and washing solutions, may be introduced into the cell compartment 12 via inlet 42 through valve 44. Nutrients are circulated through the ports 62 independently or in series as shown with hosing 64 connecting the upper nutrient chamber 66 and the lower chamber 68. Inside the organ, nutrients perfuse across the membranes 32 to feed the cultured cells. Fluorogenic measurements may be taken by opening valve 46 while the nutrients are cycled through the organ. The perfusion flow provides a steady efflux stream flowing out of port 48.

The culturing apparatus of my invention can take a variety of other forms. Capillaries may be formed of any of a variety of semi-permeable materials, such as cellulose acetate, polycarbonates, polysulfone, or acrylic copolymers, and may be coated with materials such as collagen to promote cell attachment, if desired. Capillaries are available from a variety of manufacturers including Amicon Corporation. Dow Chemical Corporation, Flow Laboratories or Bio-Rad Laboratories and have selectively permeable thin walls permitting unhindered passage of electrolytes, salts, dissolved gases, and therapeutic agents while restricting macromolecules of 10,000 to 100,000 daltons. They typically have walls 25-75 microns thick and have internal diameters of about 200 microns. Additionally, companies such as Ethicon, Inc., Millipore Corporation, Nucleopore Corporation and others manufacture membrane surfaces having similar selectively permeable walls. Preferably, the capillary or membrane material should exhibit low absorption of the fluorogenic substrate since absorption and spontaneous hydrolysis will lead to higher background fluorescence. In addition, the volume of the organ is preferrably small, i.e., a capacity for 2000 to 100,000 cultured cells should suffice.

Figure 3:
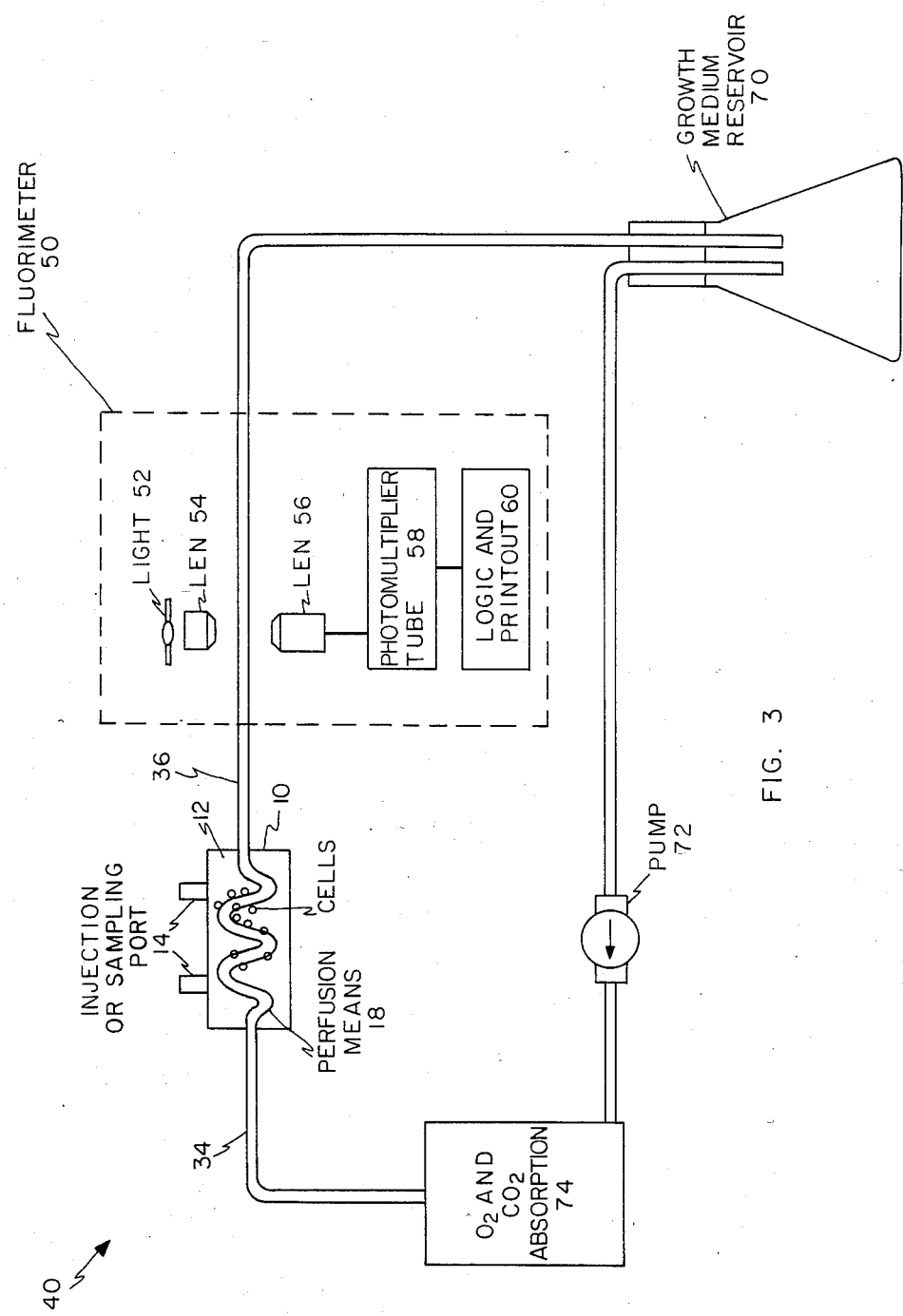
FIG. 3 is a schematic drawing of the culture assaying system of my invention.

In FIG. 3, one embodiment of the fluorochromatic system 40 of my invention is shown. Organ 10, comprising perfusion means 18 and cell compartment 12 may be innoculated with cells via ports 14. The cells are provided with nutrients and the agents to be tested via the influx stream 34 while the efflux stream 36 is monitored by fluorimeter 50. Typically, the fluorimeter 50 comprises a light source 52, focusing lens 54 and 56, a photomultiplier tube 58 and associated computational and display means 60 (which may be built-in or separate).

After passing through the fluorimeter 50, the efflux stream 36 then returns to a reservoir 70 where the nutrients are replenished and then is pumped via pump 72 through a gas diffusion means 74 (silicone tubing may be used to provide oxygen and carbon dioxide to the growth medium) and returned to the organ 10 as influx stream 34. Alternatively, fluorimeter samples may be taken from port 14 or 16. The organ may be enclosed in an incubator (not shown) to control organ temperature.

Agents to be tested may be introduced directly into the cell compartment via ports 14, or indirectly via the influx stream 34 or by adding the agent to the growth medium reservoir 70 (which is preferred for obtaining dilutions comparable with in vivo conditions). If necessary the cells can be removed from the organ by enzyme detachment (i.e., interior circulation of trypsin) and flushing.

In one set of experiments the system of FIG. 3 was tested using a commercially available capillary device (Amicon Vitafiber(R) 3×50 Model) as the culturing organ. Although the Amicon device had more capillaries than necessary, the acrylic copolymer capillaries performed well in passing minimal Eagle Medium (MEM) and fluorogenic substrate to cultured myeloma cells. Fluorescein monoacetate (FMA) was used as the substrate rather than fluorescein diacetate (FDA) because FDA produced background fluorescence due to nonspecific absorption and hydrolysis at the highly hydrophobic capillaries. This problem was alleviated by the use of FMA which has a free carboxyl group and is considerably more polar. (Previous studies has shown that FMA is as good a substrate as FDA but its use has been limited due to its intrinsic fluorescence; in my method, however, the FMA fluorescence is not bothersome but rather may be used to monitor FMA concentration). In other applications, it may be preferred to use fluorescein derivatives or fluorogenic substrates in conjunction with less capillaries or less absorbent capillary materials.

The organ culture formed by the Amicon 3×50 device permitted perfusion of molecules up to 50,000 daltons and the fluid in the cell compartment was driven by the pressure generated inside the fibers. This condition was found to be more favorable for sampling in the cell compartment without disturbing the cells. In other applications, less or more permeable nutrient-circulating means may be preferred. Using FMA as a fluorogenic substrate, substantial fluorochromatic differences were observed between devices containing live cells and controls.

A protocol was established whereby the fluorogenic substrate was introduced at room temperature and then most of the initial fluorescence washed away. After washing the unit was shifted to 37° C. and the kinetics of fluorescein efflux monitored. The rationale for this step was that cells excrete fluorescein 10 times faster at 37° C. rather than 27° C. while the rate of residual fluorescence shed by the capillary fibers was less affected by temperature. The test agent was then introduced and the steps of introducing the fluorogenic substrate, washing and monitoring repeated with changes in the fluorochromatic kinetics noted.

In FIG. 4, the results of treatment with formaldehyde and methotrexate are shown. The darkened dots indicate measurements of fluorescence taken with the system described above before any agent was introduced (base-line data) while the while centered dots indicate fluorochromatic kinetics after treatment with formaldehyde. As can be seen, the living cell culture exhibited a large spike of excreted fluorescence as soon as the temperature was increased to 37° C. Once exposed to the agent, the culture showed significantly less fluorescence after the temperature shift, indicating that the agent was effective in killing the cells and the culture was no longer able to exhibit fluorochromasia. The results of this experiment were confirmed by visual observations of the cells using conventional viability tests after removing them from the organ. The darkened boxes indicate fluorochromatic kinetics after treatment of a similar organ unit with a methotrexate agent (0.9 micrograms per milliliter) for 36 hours.

In clinical use my system entails the distribution of a biopsy sample into one or more culture organs. Once the cultures grow to steady state conditions, a base-line or unit profile is obtained for each unit. (The base-line may vary due to the number and composition of cells). After profiling, the drugs to be tested are introduced into the units and changes in the profile reflect the sensitivity of the cell cultures to each drug. If no effects (or minimal effects) are observed, then different drugs, higher doses or synergistic combinations may be tested using the same units again.

What I claim is:

1. A method of assaying the sensitivity of biopsied cells to therapeutic agents, the method comprising:
    (a) culturing the cells in a cell culturing apparatus which comprises either at least one semi-permeable membrane surface or at least one semi-permeable capillary vessel which enables the perfusion of nutrients to the biopsied cells;
    (b) contacting the cells with a fluorogenic substrate, whereby living cells release an initial characteristic amount of fluorescence;
    (c) measuring said initial fluorescence to establish a baseline;
    (d) introducing the agent into the culturing apparatus; and
    (e) measuring changes in the fluorescence released by the cells as an indicator of the sensitivity of the cells to the agent.

2. The method of claim 1 wherein the step of measuring changes in fluorescence further comprises comparing the baseline measurement with a second measurement of released fluorescence after a second contact with the substrate subsequent to introducing the agent.

3. The method of claim 1 wherein changes in fluorescence are determined by measuring changes in fluorescent activity.

4. The method of claim 1 wherein changes in fluorescence are measured kinetically.

5. The method of claim 1 wherein the method further comprises varying the temperature of the culturing apparatus prior to measuring changes in fluorescence.

6. The method of claim 1 wherein the fluorogenic substrate is a fluorescein containing compound which liberates fluorescein when hydrolyzed by cells.

7. The method of claim 1 wherein cells are contacted with at least one substrate chosen from the group of fluorescein diacetate, fluorescein monoacetate and derivatives thereof, wherein fluorescein is liberated when hydrolyzed by cells.

8. The method of claim 1 wherein the cell culturing apparatus comprises at least one semi-permeable capillary vessel which enables the perfusion of nutrients to the biopsied cells.

9. The method of claim 1 wherein the cell culturing apparatus comprises at least one semi-permeable membrane surface which enables the perfusion of nutrients to the biopsied cells.

10. The method of claim 1 wherein the artificial cell culturing apparatus comprises a cell compartment which provides for influx of an oxygenated medium and changes in the fluorescence are detected by changes in nutrient medium exiting the cell compartment.

* * * * *